United States Patent
Wallock et al.

(10) Patent No.: US 7,163,245 B2
(45) Date of Patent: Jan. 16, 2007

(54) CONTACT LENS INSERTION TOOL

(76) Inventors: Ollie Wallock, 117 Winton St., Springfield, MA (US) 01118; John Dalsey, 77 Emerson Rd., Longmeadow, MA (US) 01106

( * ) Notice: Subject to any disclaimer, the term of this patent is extended or adjusted under 35 U.S.C. 154(b) by 0 days.

(21) Appl. No.: 10/795,074

(22) Filed: Mar. 4, 2004

(65) Prior Publication Data

US 2005/0194798 A1    Sep. 8, 2005

(51) Int. Cl.
*A61F 9/00* (2006.01)
(52) U.S. Cl. ........................ 294/1.2; 294/64.1
(58) Field of Classification Search ............... 294/1.2, 294/64.1; 606/166, 107; 206/5.1
See application file for complete search history.

(56) References Cited

U.S. PATENT DOCUMENTS

| | | | |
|---|---|---|---|
| 3,304,113 A | | 2/1967 | Hutchison |
| 3,600,028 A | | 8/1971 | Henning |
| 3,743,337 A | * | 7/1973 | Crary ..................... 294/1.2 |
| 3,791,689 A | * | 2/1974 | Boone et al. ............. 294/1.2 |
| 3,934,914 A | | 1/1976 | Carruthers |
| 4,026,591 A | | 5/1977 | Cleaveland |
| 4,093,291 A | | 6/1978 | Schurgin |
| 4,201,408 A | | 5/1980 | Tressel |
| 4,378,126 A | * | 3/1983 | Procenko ................. 294/1.2 |
| 5,788,706 A | | 8/1998 | Deminski |
| 5,929,968 A | | 7/1999 | Cotie et al. |

* cited by examiner

*Primary Examiner*—Gene O Crawford
*Assistant Examiner*—Esther Onyinyechi Okezie
(74) *Attorney, Agent, or Firm*—McCormick, Paulding & Huber LLP

(57) ABSTRACT

An insertion tool of the present invention includes a housing shaped to accommodate a generated light source and a power source. The generated light source is electrically connected to the power source and projects a beam of light along an axis toward a distal end of the housing. The insertion tool also includes a lens holder attached to the distal end of the housing. The lens holder has an opening that allows the beam of light to pass through the housing and lens holder. The beam of light is visible to a wearer when the lens holder is aligned with the wearer's eye. The invention uses the strategy of focusing on a target that can be clearly seen by the user to insert a lens that otherwise can't be seen by the user.

9 Claims, 3 Drawing Sheets

CONTACT LENS INSERTION TOOL

FIELD OF THE INVENTION

The present invention relates generally to an apparatus for the insertion of contact lenses. More particularly, the present invention relates to an insertion tool that utilizes generated light so that a wearer can easily align a contact lens with the wearer's eye.

BACKGROUND OF THE INVENTION

Individuals who are functionally blind due to eye injuries or diseases of the cornea often use rigid gas permeable ("RPG") contact lenses. In particular, such individuals often utilize a Scleral TM lens, which is frequently referred to as a "bandaged" lens.

When inserting an RGP lens, or a Scleral TM lens which contains a large volume of fluid, it is critical that the user keep the lens aligned with the user's eye. The alignment involves both centering the lens on the eye and aligning the lens on a perpendicular axis to the eye. The lens must be centered and square to the eye for a successful insertion.

If a Scleral TM lens is misaligned during insertion, the fluid may spill out. Moreover, a slight misalignment of an RPG or Scleral TM lens may cause the lens to hit the user's eyelid or finger and fall out. Additionally, insertion of a lens such that it is only partly on the cornea or in the corner of the eye can cause injury. Flinching, blinking or premature closing of the eye at insertion can also cause insertion failures. Even if an imperfect alignment does not cause injury but aligns by flipping onto the sclera, there is a good chance that bubbles will be formed in the fluid reducing the efficacy of the lens.

Typically, when inserting such lenses, a user will employ a mirror or other means to align the lens with an eye. Users with low vision, however, have great difficulty using a mirror or other method in which they must visualize the lens to align it for insertion. Moreover, even with regular contact lenses, i.e., non-RPG or Scleral TM lenses, alignment is difficult or impossible to achieve when the lens is very close to the user's eye. Additionally, lens wearers tend to look away from the lens at the moment of insertion. When a wearer looks away from the lens, the lens is often inserted in a misaligned state.

The present invention addresses the above-identified problems. The present invention utilizes a generated light source that is focused and projected upward from the bottom surface of a hollow plunger to facilitate alignment. The light is projected upward through the inner cavity of the plunger and through an opening in the lens holder attached to the plunger. If a user looking into the hollow plunger can see the light coming up from the bottom of the plunger through the opening in the lens holder, then the device and lens are both centered, perpendicular to the eye and ready for insertion. Furthermore, the user must focus on the light and the lens during the insertion process, reducing the probability of the user looking away from the lens at the moment of insertion.

Moreover, the present invention also assists an individual, such as a trainer or physician, in inserting a lens into a patient's eye. When an inserter uses the tool to install a lens, the light coming out of the plunger can be seen on the patient's eye. If the patient can see the light coming from the bottom of the plunger at the same time the inserter can see the light on the center of the eye, then the light beam has sighted the center of the eye and the lens is square to the eye. For the trainer who is observing the patient insert a lens, especially during the first solo attempts, he or she can observe whether the insertion process is on track by looking at the beam shining on the eye. The feedback allows the trainer to evaluate the patient's insertion technique and make any required adjustments in the technique prior to an improper insertion. This combined with the automatic feedback of the user substantially decreases training time. The feedback causes the user to constantly adjust the device and the head to remain focused on the light at the end of the plunger.

The present invention utilizes a targeting or "gun barrel" effect to achieve alignment. The placement of a light source at the bottom of the inner cavity of the plunger and the configuration of the lens holder creates this effect. If a user sees the light at all, or sees light in the center of the field of light, depending on how the device is made the lens is perfectly aligned and ready to insert. The device holds the lens firm through suction.

Additionally, the present invention overcomes significant drawbacks of the prior art that have attempted to address the above-identified problems. Prior art insertion devices generally employ a light located on the top surface of the insertion tool close to the eye of the contact wearer, which creates no targeting effect and does not assist in alignment as does the present invention.

Other prior art devices, such as the handling tool disclosed in U.S. Pat. No. 4,026,591, hereby incorporated by reference in its entirety, employ a natural light source, i.e. the ambient light in a room, to guide alignment. This light is insufficient for those with low vision and is likely insufficient for all contact wearers in low light or changing light environments. To compensate for this significant shortcoming, the prior art handling tool includes a large, complex eye cup and steady rest which contact the face of the user to ensure alignment. The present invention overcomes this drawback by proposing an insertion tool that provides a beam of generated light travelling along an inner longitudinal axis of the tool that is clearly visible to individuals with low vision.

SUMMARY OF THE INVENTION

It is an object of the present invention to provide an insertion device that allows an individual with low vision to easily align and insert a contact lens.

It is a further object of the present invention to provide an insertion device that allows an individual to easily align and insert a lens in another person's eye.

It is an additional object of the present invention to provide an insertion device with a light source that can be sterilized.

It is yet another object of the present invention to provide an insertion device that allows the user to continue to look at the light throughout the insertion process, thereby eliminating failures due to flinching, blinking or premature closing of the eye.

A preferred embodiment of the insertion tool of the present invention includes a housing shaped to accommodate a generated light source and a power source. The generated light source projects a beam of light along an axis toward a distal end of the housing. The insertion tool also includes a lens holder attached to the distal end of the housing. The lens holder has an opening that allows the beam of light to pass through the housing and lens holder. The beam of light is visible to a user when the lens holder is aligned with the user's eye.

This and other objects and advantages of this invention will be more readily appreciated from a reading of the application in conjunction with the drawings annexed hereto as follows.

DETAILED DESCRIPTION OF THE PREFERRED EMBODIMENT

Figure 1:
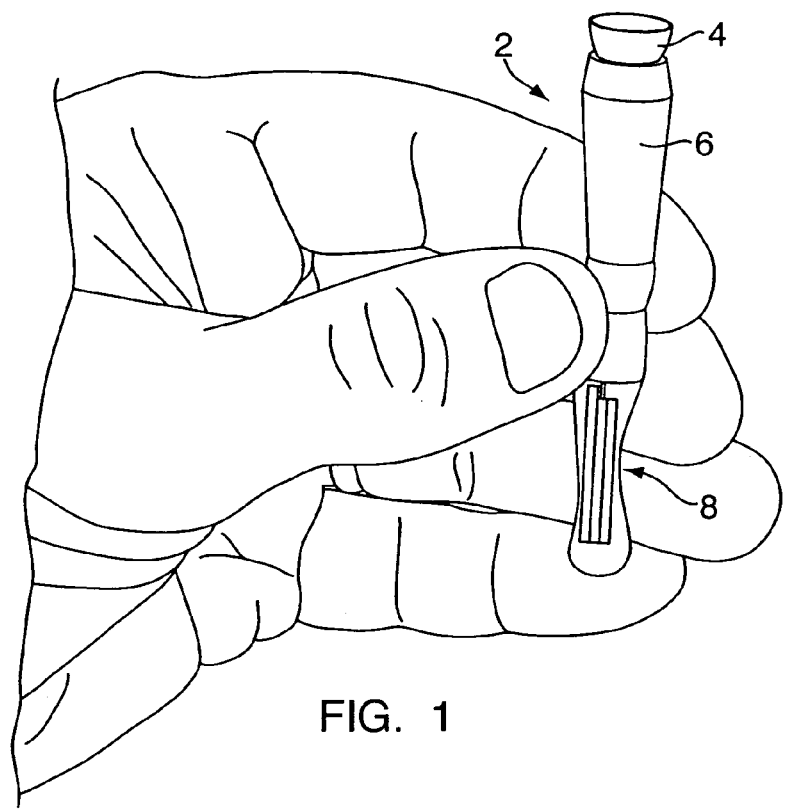
FIG. 1 is a side view of an insertion tool of the present invention.

Referring to FIG. 1, a preferred embodiment of the insertion device 2 of the present invention includes a lens holder 4, a plunger 6 and a housing 8. The plunger 6 is attached to a distal end of the housing 8. In a preferred embodiment, the housing 8 is selectively removable from the plunger 6 and is water-proof or water resistant such that it may be cleaned without damaging the contents of the housing, which are discussed in detail below. Additionally, the housing is water-resistant such that lens fluid may contact the housing without damaging its contents.

Figure 2:
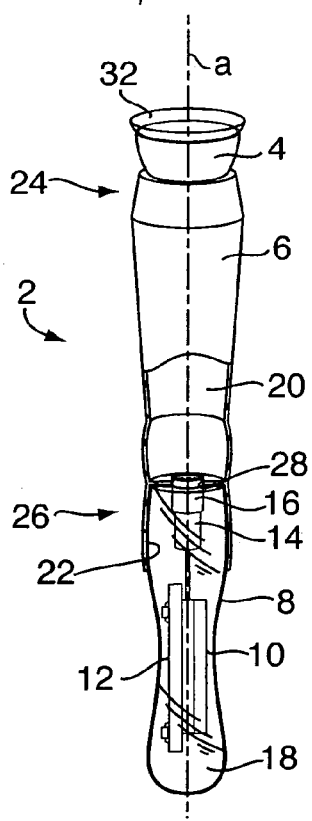
FIG. 2 is a partially cut-away side view of the insertion tool of FIG. 1.

Referring now to FIG. 2, the housing 8 has an inner cavity 18 that contains a power source 10, a generated light source 14, a light conduit 16 that is sealed to the air. The light conduit 16 may be a fiber optic lens and/or tube 16 to focus and transmit the light emitted from the generated light source. The housing further includes a circuit 12 for controlling the light source. Preferably, the circuit 12 also includes an integrated switch such that a user can selectively energize the circuit 12 and the generated light source. The power source may be a lithium or silver oxide watch-type battery although other power sources may be employed without departing form the broader aspects of the present invention. The insertion device 2 has an illumination axis α along which the beam of light is emitted and focused. The embodiment shown uses batteries along with a circuit that controls the power to the light source; in this case, a light emitting diode.

An important aspect of the insertion tool 2 of the present invention is the use of a generated light source 14 that emits a beam of light along the illumination axis α. Prior art insertion tools utilize a natural light source, i.e. the ambient light in a room, to guide alignment. Ambient light, however, is insufficient for those with low vision and is likely insufficient for all contact wearers in low light or changing light environments. The generated light source of the present invention allows insertion of a contact lens in varying levels of background light. Additionally, the present invention allows insertion of a lens by wearer's with varying degrees of vision and without the aid of a mirror.

Returning now to FIG. 2, the housing 8 may be cleaned without damaging the contents of the inner cavity 18. The generated light source 14 may be a light emitting diode, a bulb or a laser light source.

The plunger 6 has two ends, a first or front end 24 on which the lens holder 4 is formed and a second or rear end 26 to which the distal end of the housing 8 is attached. The plunger 6 has a housing opening or recess 22 in its rear end into which the distal end of the housing 8 fits. Preferably, the opening 22 is configured such that it forms a sleeve over the housing 8 accommodating the housing 8 within the plunger 6. The plunger 6 further includes an inner cavity 20. The inner cavity 20 is separated from the housing opening 22 by a rear wall within which a lens opening 28 is defined to accommodate the fiber optic lens and/or tube 16 allowing the focused light to pass into from the housing 8 into the plunger 6 along the axis α.

Another important aspect of the present invention is the fact that the generated light source 14 emits a beam of light along the illumination axis α through the plunger 6. By passing through the inner cavity 20 of the plunger 6, a channeling or targeting effect is created allowing a user to align the insertion tool 2 by tilting the tool 2 until the beam of light is visible or centered.

Referring back to FIG. 2, the plunger 6 is manufactured from a soft plastic or rubber material such that it may be easily deformed and compressed to create a suction effect thereby securing the lens 32 to the lens holder 4. The plunger 6 may be detached from the housing 8 such that the component are easily cleaned and/or replaced.

An additional important aspect of the present invention is that the insertion device 2 has a plunger 6 that may be easily compressed by a user with one hand. Prior art devices utilize more elaborate plungers that include handles. Such devices require the use of both hands of the user, one hand to hold the device to the user's eye and the other hand to depress the plunger. The plunger 6 of the present invention is attached to the housing 8 such that to utilize the insertion tool 2, a user grips the tool 2 by the plunger 6 and may compress the plunger 6 with his or her gripping hand.

Figure 3:
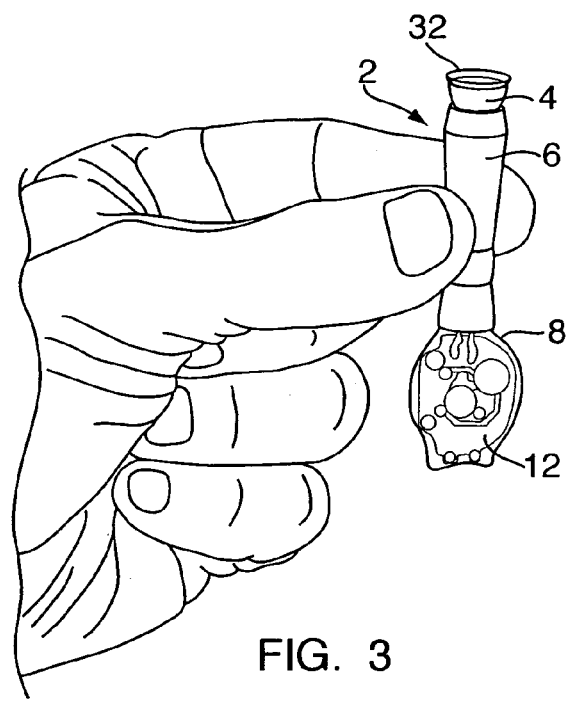
FIG. 3 is a front view of the insertion tool of FIG. 1, depicting a circuit controlling the light source.
Figure 4:
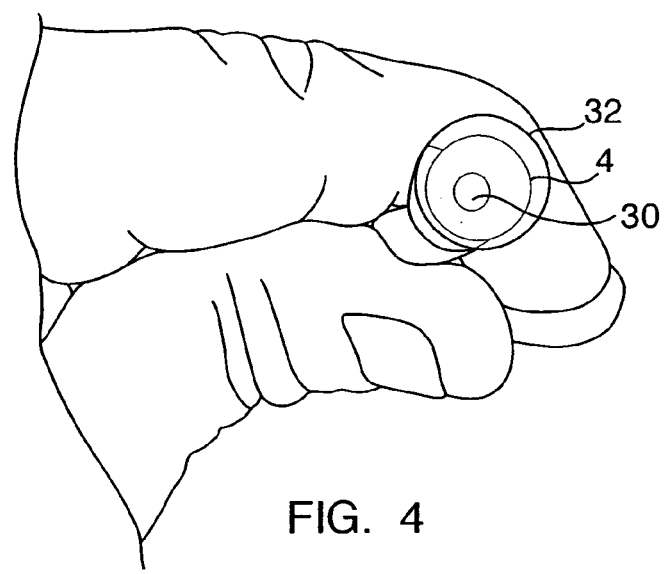
FIG. 4 is an enlarged top view of the insertion tool of the present invention in a misaligned condition.

Referring now to FIGS. 3 and 4, the lens holder 4 is formed on the upper end of the plunger 6. The lens holder 4 is semi-spherical and substantially concave and has a center portion containing an annular opening 30 that allows a user to look into the plunger 6 and view the light emanating from the generated light source along the illumination axis α. As will be appreciated, the lens holder 4 is designed to accommodate a lens 32. As mentioned previously, the lens 32 is secured to the lens holder 4 through suction created by manually compressing the plunger 6 longitudinally. The suction and shape of the lens holder 4 are designed to hold the lens 32 square to the insertion tool 2. When the lens 32 is positioned correctly, the user or wearer may release his or her compression of the plunger 6 and seat the lens 32 on the user's eye.

When the insertion device 2 is in use, the light from the generated light source 14 is focused along illumination axis α. The light is projected along this axis through the inner cavity 20 of the plunger 6 and may be viewed through the annular opening in the lens holder 4. By placing the light source toward the bottom of the plunger 6, a targeting or "gun barrel" effect is created. When the light is fully visible in the annular opening 30 of the lens holder 4, the insertion tool 2 and lens 32 are perpendicular to the user's eye.

Figure 5:
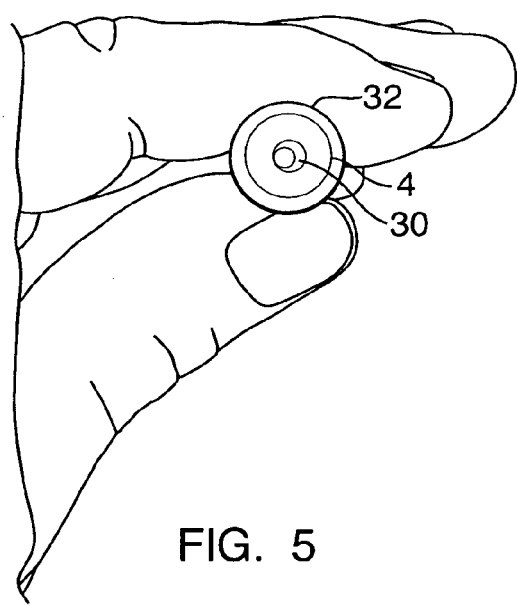
FIG. 5 is an additional enlarged top view of the insertion tool of the present invention showing the tool in a misaligned condition though approaching alignment.
Figure 6:
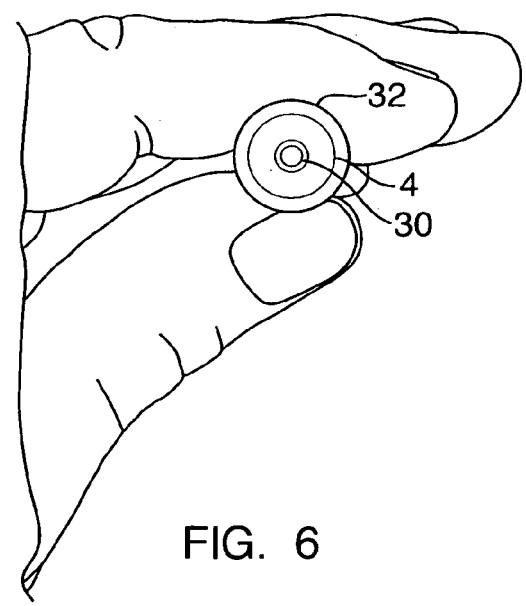
FIG. 6 is an additional enlarged top view of the insertion tool of the present invention in an aligned state.

FIGS. 4–6 are all top views of the insertion tool 2 of the present invention with a lens 32 on the lens holder 4. The Figures depict the insertion tool 2 in various states of alignment with a wearer's eye. FIG. 4 depicts the insertion tool 2 is a state of misalignment. When the tool 2 is misaligned, no light is seen through the annular opening 30 in the lens holder 4 indicating that the lens 32 may not be inserted in the wearer's eye.

FIG. 5 illustrates the insertion tool 2 nearing alignment with a wearer's eye. The light is partially visible through the annular opening 30 in the lens holder 4.

Turning now to FIG. 6, the insertion tool 2 is completely aligned with the user's eye. The light from the generated light source 14 is entirely visible in the center of the annular opening 30 of the lens holder 4. The lens 32 is now ready for insertion in the wearer's eye.

Alternatively, instead of a completely centered light beam indicating alignment, the insertion tool 2 can be configured such that the light is either not visible, indicating a state of misalignment, or visible indication a state of alignment.

Figure 7:
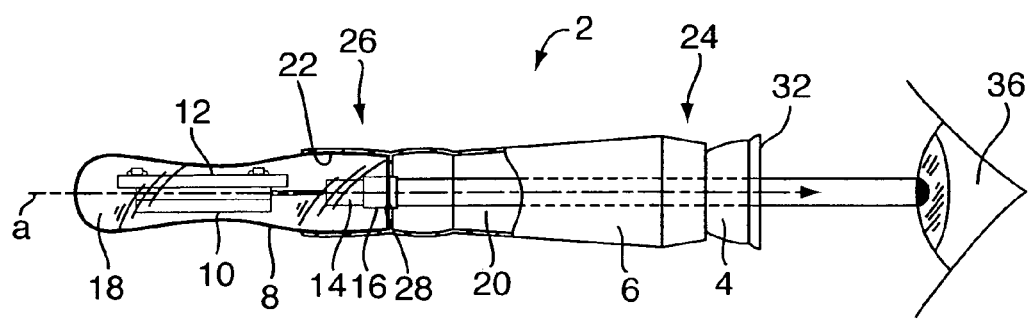
FIG. 7 is a partially cut-away side view of the insertion tool of FIG. 1 illustrating the relationship between the tool and a user's eye when the tool is in a state of alignment.
Figure 8:
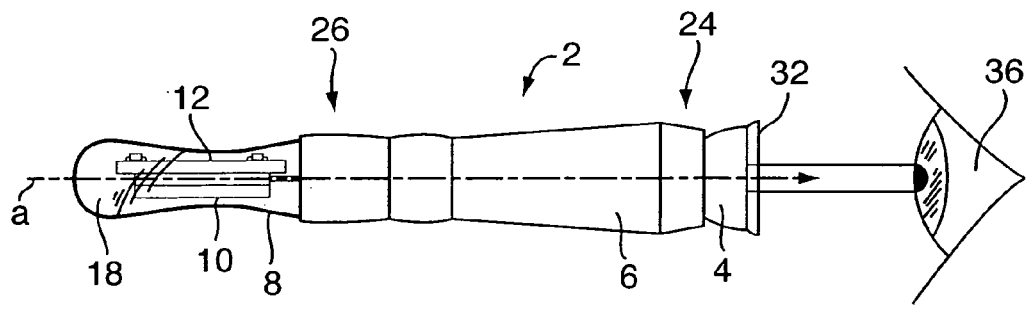
FIG. 8 is a top view of the insertion tool of FIG. 1 illustrating the relationship between the tool and a user's eye when the tool is in a state of alignment.

As shown in FIGS. 7 and 8, when the insertion tool 2 is completely aligned, the beam of light 34 travels along illumination axis α and is centered on the user's eye 36 and the lens 32 is may be properly inserted.

In addition to facilitating the insertion of a lens 32 into a wearer's eye by the wearer, the present invention assists an individual, such as a trainer or physician, in inserting a lens 32 into a patient's eye. When an inserter uses the insertion tool 2 to install a lens 32, the light coming out of the plunger 6 can be seen on the patient's eye. If the patient can see the through the annular opening 30 of the lens holder 4 at the same time the inserter can see the light on the center of the eye, then the light beam has sighted the center of the eye and the lens 32 is square to the eye. For a trainer observing the patient insert a lens 32, he or she can observe whether the insertion process is on track by looking at the beam of light shining on the eye. The feedback allows the trainer to evaluate the patient's insertion technique and make any required adjustments in the technique prior to an improper insertion. The above is an important aspect of the present invention in that prior art devices do not allow for this functionality as their light sources are either not visible on the eye of the wearer or the light is not channeled or targeted.

In an alternate embodiment, the generated light source may be contained in the plunger while the power source and switch are contained in the housing. When the plunger is inserted into the housing, the generated light source is electrically connected to the power source and may be selectively actuated.

The foregoing description is intended to describe the preferred form of the invention and the best mode contemplated by me for carrying out this invention. To those skilled in the art, however, various modifications and variations to the specific embodiments described herein may be apparent without departing from the scope of my invention.

What is claimed is:

1. An insertion tool for the insertion of a contact lens onto a lens wearer's eye, said insertion tool comprising:
   a housing having a power source and a generated light source, said generated light source being disposed on a forward end of the housing;
   a plunger attached to the forward end of the housing, the plunger having a distal end, a proximal end defined by a rear wall, an inner cavity, said rear wall having an opening into which the generated light source of the housing projects a beam of light along an axis toward the distal end of the plunger, said rear wall opening having a peripheral boundary through which the beam of light projects, said peripheral boundary defining the dimensions of said beam of light;
   a lens holder attached to the distal end of said plunger, said lens holder having an opening that allows the beam of light to pass through the plunger and lens holder, said beam of light being visible to a wearer when the lens holder is aligned with the wearer's eye;
   wherein said plunger is manually compressible creating a suction effect securing a lens to said lens holder; and
   said generated light source is electrically connected to the proximal end of said plunger, said proximal end being opposite and spaced away from said distal end of said plunger, said beam of light projecting along an axis in the inner cavity that extends from said proximal end of said plunger to said distal end;
   wherein said plunger is deformable in a direction substantially perpendicular to the axis of the beam of light and wherein said beam of light is not altered by any structure located within the inner cavity; and
   wherein the entire peripheral boundary of said beam of light is visible within said opening in said lens holder allowing a user to align the insertion tool by tilting the tool until the entire peripheral boundary is visible and centered within the opening in the lens holder.

2. The insertion tool of claim 1, wherein said housing is water-resistant and removably attached to said plunger such that both the housing plunger may be easily cleaned or replaced.

3. The insertion tool of claim 1, wherein said housing further comprises a circuit and a switch electrically connected to said power source and generated light source such that a wearer may selectively project the beam of light.

4. The insertion tool of claim 1, wherein said inner cavity further comprises a fiber optic lens or tube that focuses the beam of light emitted from the generated light source, said lens or tube further defining the peripheral boundary of the beam of light.

5. The insertion tool of claim 1, wherein said plunger is tubular.

6. The insertion tool of claim 1, wherein said lens holder is an annular, substantially concave cup.

7. An insertion tool for the insertion of a Scleral or RGP contact lens onto a lens wearer's eye, said insertion tool comprising:
   a housing having a power source and a generated light source, said generated light source being disposed on a forward end of the housing, said housing is water-resistant and removably attached to a plunger such that both the housing and plunger may be easily cleaned or replaced;
   a tubular plunger attached to the forward end of the housing, the plunger having a distal end, a proximal end defined by a rear wall, an inner cavity, said rear wall having an opening into which the generated light source of the housing projects a beam of light along an axis toward the distal end of the plunger; said housing further comprising a circuit and a switch electrically connected to said power source and generated light source such that a wearer may selectively project the beam of light, said rear wall opening having a peripheral boundary through which the beam of light projects, said peripheral boundary defining the dimensions of said beam of light;
   a lens holder attached to the distal end of said plunger, said lens holder having an opening that allows the beam of light to pass through the plunger and lens holder, said opening in said lens holder being larger than the dimensions of said beam of light;

wherein said plunger is manually compressible creating a suction effect securing a lens to said lens holder;

said proximal end being opposite and spaced away from said distal end of said plunger, said beam of light projecting along an axis in the inner cavity that extends from approximately said proximal end of said plunger to said distal end; and wherein said beam of light is not altered by any structure located within the inner cavity and wherein the entire peripheral boundary of said beam is visible within said opening in said lens holder allowing a user to align the insertion tool by tilting the tool until the entire peripheral boundary is visible and centered within the opening in the lens holder.

8. The insertion tool of claim 7, wherein said inner cavity further comprises a fiber optic lens or tube that focuses the beam of light emitted from the generated light source, said lens or tube further defining the peripheral boundary of the beam of light.

9. The insertion tool of claim 7, wherein said lens holder is an annular substantially concave cup.

* * * * *